United States Patent
Putila et al.

(10) Patent No.: US 11,857,299 B2
(45) Date of Patent: Jan. 2, 2024

(54) WEARABLE HEART ACTIVITY SENSOR DEVICE

(71) Applicant: Polar Electro Oy, Kempele (FI)

(72) Inventors: Veli-Pekka Putila, Kempele (FI); Elias Pekonen, Kempele (FI)

(73) Assignee: Polar Electro Oy, Kempele (FI)

( * ) Notice: Subject to any disclaimer, the term of this patent is extended or adjusted under 35 U.S.C. 154(b) by 887 days.

(21) Appl. No.: 16/720,043

(22) Filed: Dec. 19, 2019

(65) Prior Publication Data
US 2020/0205681 A1 Jul. 2, 2020

(30) Foreign Application Priority Data

Dec. 27, 2018 (EP) .................................. 18248031
Dec. 27, 2018 (FI) .................................. 20186135

(51) Int. Cl.
*A61B 5/024* (2006.01)

(52) U.S. Cl.
CPC ...... *A61B 5/02427* (2013.01); *A61B 5/02438* (2013.01); *A61B 2560/0468* (2013.01); *A61B 2562/04* (2013.01); *A61B 2562/164* (2013.01)

(58) Field of Classification Search
CPC .............. A61B 5/02427; A61B 5/6833; A61B 2562/164
See application file for complete search history.

(56) References Cited

U.S. PATENT DOCUMENTS

| | | | | |
|---|---|---|---|---|
| 10,064,282 | B2* | 8/2018 | Heikkinen | H05K 1/0298 |
| 10,383,232 | B2* | 8/2019 | Heikkinen | H10K 77/111 |
| 10,602,937 | B2* | 3/2020 | Pekonen | A61B 5/02427 |
| 11,278,245 | B2* | 3/2022 | Pekonen | A61B 5/282 |
| 11,553,881 | B2* | 1/2023 | Raso | A61B 5/02416 |
| 2005/0197583 | A1 | 9/2005 | Chance | |

(Continued)

FOREIGN PATENT DOCUMENTS

| | | |
|---|---|---|
| WO | 2015/176999 A1 | 11/2015 |
| WO | 2017/182677 A2 | 10/2017 |
| WO | 2017/182677 A3 | 10/2017 |

OTHER PUBLICATIONS

Extended European Search Report received for European Patent Application Serial No. 18248031.9 dated Jun. 13, 2019, 9 pages.

(Continued)

*Primary Examiner* — Carl H Layno
*Assistant Examiner* — Manolis Pahakis
(74) *Attorney, Agent, or Firm* — FisherBroyles, LLP

(57) ABSTRACT

A wearable heart activity sensor device includes a substrate of optically transparent material arranged to face a skin of a user when the sensor device is worn by the user, at least one light emitting diode, LED, arranged on the substrate and arranged to emit light through the substrate, at least one photo sensor arranged on the substrate as spatially separated from the at least one LED and arranged to absorb light through the substrate, wherein the at least one LED and the at least one photo sensor are included in a photoplethysmogram sensor of the heart activity sensor device, and an overmold of thermoplastic material covering the at least one light emitting diode, the at least one photo sensor and a space between the at least one light emitting diode and the at least one photo sensor.

12 Claims, 8 Drawing Sheets

900: 1ST SET OF LEDS

902: 2ND SET OF LEDS

904: PHOTODIODE

(56) References Cited

U.S. PATENT DOCUMENTS

| | | | |
|---|---|---|---|
| 2006/0028837 A1* | 2/2006 | Mrakovich | G02B 6/001 |
| | | | 362/602 |
| 2007/0121326 A1* | 5/2007 | Nall | F21V 3/12 |
| | | | 362/294 |
| 2010/0030088 A1 | 2/2010 | Carney et al. | |
| 2014/0257060 A1* | 9/2014 | Petersen | A61B 5/0015 |
| | | | 600/323 |
| 2014/0275884 A1* | 9/2014 | Lin | A61B 5/6838 |
| | | | 600/324 |
| 2015/0223716 A1 | 8/2015 | Korkala et al. | |
| 2015/0342480 A1* | 12/2015 | Justice | A61B 5/681 |
| | | | 600/479 |
| 2015/0342529 A1* | 12/2015 | Gassoway | A61B 5/6831 |
| | | | 600/479 |
| 2016/0029911 A1* | 2/2016 | Lee | A61B 5/02427 |
| | | | 600/407 |
| 2016/0374621 A1* | 12/2016 | LeBoeuf | A61B 5/6803 |
| | | | 600/476 |
| 2017/0021172 A1* | 1/2017 | Perez | A61N 1/37211 |
| 2018/0000363 A1 | 1/2018 | Pekonen et al. | |
| 2018/0085580 A1* | 3/2018 | Perez | A61N 1/36014 |
| 2018/0177459 A1* | 6/2018 | Eletr | A61B 5/02125 |
| 2018/0279924 A1 | 10/2018 | Kuhn | |
| 2018/0310846 A1 | 11/2018 | Lin | |
| 2020/0113460 A1* | 4/2020 | Gomo | A61B 5/6823 |
| 2020/0371598 A1* | 11/2020 | Sadarangani | A61B 5/0295 |
| 2022/0007954 A1* | 1/2022 | Korkala | A61B 5/14552 |

OTHER PUBLICATIONS

Finnish Patent Search Report received for Finnish Patent Application Serial No. 2086135 dated Jul. 19, 2019, 2 pages.

* cited by examiner

WEARABLE HEART ACTIVITY SENSOR DEVICE

CROSS-REFERENCE TO RELATED APPLICATIONS

This application claims benefit and priority to European Application No. 18248031.9, filed Dec. 27, 2018, and Finnish Application No. 20186135, filed Dec. 27, 2018, which are incorporated by reference herein in their entireties.

BACKGROUND

Field

The present invention relates to a field of physiological or biometric measurements and, in particular, to a structure of a wearable heart activity sensor device.

Description of The Related Art

A (PPG) sensor is an example of a heart activity sensor. A PPG sensor conventionally comprises at least one light source, such as a light emitting diode (LED), and at least one photo sensor such as a photodiode. Light emitted by the LED(s) is directed to a skin of a user wearing the PPG sensor, and the light is delivered via the skin to the photodiode(s). For the accurate PPG measurements, it is important to deliver the light from the LED(s) to the photodiode(s) via the skin. Any light delivered from the LED(s) to the photodiode(s) is interference.

A conventional way of manufacturing such a sensor is to assemble the LED(s) and the photodiode(s) on a substrate and assemble separate optical barriers between the LED(s) and the photodiode(s) to direct the light to the skin.

SUMMARY

According to an aspect, there is provided a wearable heart activity sensor device comprising: a substrate of optically transparent material arranged to face a skin of a user when the sensor device is worn by the user; at least one light emitting diode, LED, arranged on the substrate and arranged to emit light through the substrate; at least one photo sensor arranged on the substrate as spatially separated from the at least one LED and arranged to absorb light through the substrate, wherein the at least one LED and the at least one photo sensor are comprised in a photoplethysmogram sensor of the heart activity sensor device; and an overmold of thermoplastic material covering the at least one light emitting diode, the at least one photo sensor and a space between the at least one light emitting diode and the at least one photo sensor.

In an embodiment, the overmold of thermoplastic material is optically non-transparent.

In an embodiment, the device further comprises at least one skin measurement electrode arranged on the substrate on the opposite side than the at least one LED and the at least one photo sensor.

In an embodiment, the substrate comprises at least one through hole for a signal line to the at least one electrode.

In an embodiment, thickness of the substrate is 0.76 millimetres or less.

In an embodiment, the substrate is of flexible material, and wherein the overmold of thermoplastic material is rigid.

In an embodiment, the device further comprises: at least one processor external to the overmold of thermoplastic material; and signal lines arranged on the substrate inside and outside the overmold to couple the at least one processor to the at least one light emitting diode and the at least one photo sensor.

In an embodiment, the at least one LED comprises a first set of LEDs arranged to emit light at a first wavelength and a second set of LEDs arranged to emit light at a first wavelength different from the first wavelength, and wherein the first set and second set of LEDs are arranged spatially in pairs such that each pair comprises a LED of the first set and a LED of the second set disposed directly next to one another on the substrate, wherein different pairs of LEDs are spatially separated on the substrate, and wherein the overmold covers a space between the different pairs of LEDs.

In an embodiment, the pairs of LEDs are disposed to different directions from the at least one photo sensor.

In an embodiment, the at least one photo sensor comprises a plurality of photo sensors, wherein at least one pair of LEDs is disposed between the plurality of photo sensors, and wherein at least two pairs of LEDs are disposed between opposite sides of one of the plurality of photo sensors.

In an embodiment, the device further comprises at least one display screen on the substrate, wherein the overmold covers the at least one display screen and at least the part of the overmold that covers the display screen is of optically transparent material.

According to another aspect, there is provided a method for manufacturing a wearable heart activity sensor device, comprising: obtaining a substrate of optically transparent material; assembling at least one light emitting diode, LED, of a photoplehysmogram, PPG, sensor on the substrate such that the at least one LED is arranged to emit light through the substrate; assembling at least one photo sensor of the PPG sensor on the substrate as spatially separated from the at least one LED and such that the at least one photo sensor is arranged to absorb light emitted by the at least one LED through the substrate; and overmolding the at least one light emitting diode, the at least one photo sensor and a space between the at least one light emitting diode and the at least one photo sensor with thermoplastic material.

In an embodiment, the method further comprises: assembling at least one skin measurement electrode on the substrate on the opposite side than the at least one LED and the at least one photo sensor; forming at least one through hole to the substrate; and arranging a signal line to the at least one electrode through the at least one through hole.

In an embodiment, the method further comprises: arranging a plurality of signal lines on the substrate, the plurality of signal lines coupling to the at least one LED and the at least one photo sensor; arranging the overmold to cover the signal lines only partially; and after said overmolding, coupling exposed parts of the signal lines to at least one electronic component external to the overmold.

In an embodiment, the method further comprises thermoforming the substrate before assembling the at least one LED and the at least one photo sensor on the substrate.

BRIEF DESCRIPTION OF THE DRAWINGS

In the following the invention will be described in greater detail by means of preferred embodiments with reference to the attached [accompanying] drawings, in which.

DETAILED DESCRIPTION

The following embodiments are exemplifying. Although the specification may refer to "an", "one", or "some" embodiment(s) in several locations of the text, this does not necessarily mean that each reference is made to the same embodiment(s), or that a particular feature only applies to a single embodiment. Single features of different embodiments may also be combined to provide other embodiments.

Figure 1:
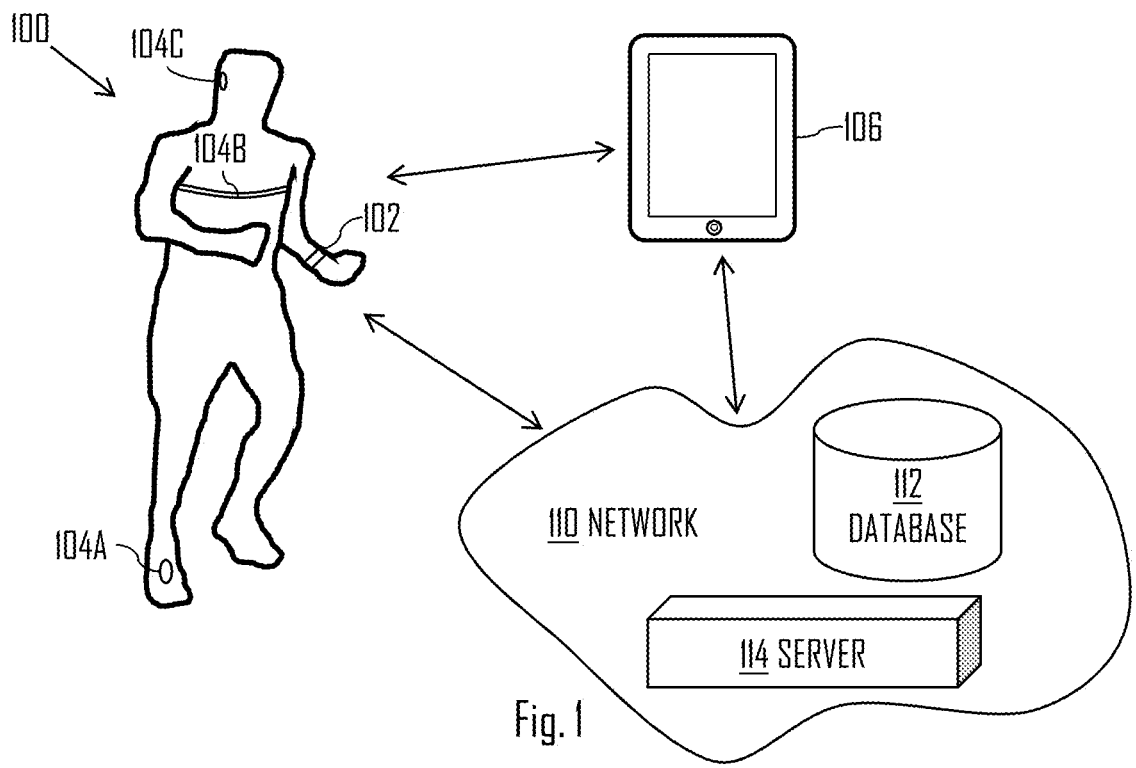
FIG. 1 illustrates sensor devices to which embodiments of the invention may be applied.

FIG. 1 illustrates a system to which embodiments of the invention may be applied. Said system may be used to monitor physical training, activity, and/or inactivity of a user 100. Thus, the embodiments may not be limited to monitoring and/or measuring physical training of the user 100, and thus said system may be used to monitor physical activity and/or inactivity during the day and/or night (e.g. 24 hours a day). Such may be possible by using one or more devices described with respect to FIG. 1 and in the embodiments below.

Referring to FIG. 1, the user 100 may wear a wearable device, such as a wrist device 102, a head sensor unit 104C, a torso sensor 104B, and/or a leg sensor 104A. In another example, the wearable device may be and/or be comprised in glasses. In another example, the wearable device is comprised or configured to be coupled with a garment or garments (or apparel). Examples of such garments may include bra(s), swimming apparel, such as swimming suit or cap, and glove(s). The garment or apparel may be worn by the user. In some embodiments, the wearable device is integrated as a part of the garment or apparel. Due to simplicity reasons, let us now describe the wearable device as being the wrist device 102. However, embodiments described in relation to wrist device 102 may be utilized by other types of wearable devices, i.e. the embodiments are not necessarily limited to wrist device or devices 102.

The wrist device 102 may be, for example, a smart watch, a smart device, sports watch, and/or an activity tracking apparatus (e.g. bracelet, arm band, wrist band, mobile phone). The wrist device 102 may be used to monitor physical activity of the user 100 by using data from internal sensor(s) comprised in the wrist device 102 data from external sensor device(s) 104A-C, and/or data from external services (e.g. training database 112). It may be possible to receive physical-activity-related information from a network 110, as the network may comprise, for example, physical activity-related information of the user 100 and/or some other user(s). Thus, the wrist device 102 may be used to monitor physical activity related information of the user 100 and/or the other user(s). Naturally, one or more of the external sensor device(s) 104A-C may be worn by the other user(s), and thus information received from said one or more sensor device(s) 104A-C may be monitored from the wrist device 102 by the user 100. The network 110 may comprise the training database 112 and/or the server 114. The server 114 may be configured to enable data transfer between the training database 112 and some external device, such as the wearable device. Hence, the database 112 may be used to store cardiac activity measurement data, for example.

It needs to be understood that the wrist device 102 may be used to monitor physical activity of the user 100 and/or to be used as a smart watch configured to enable communication with, for example, a portable electronic device 106, the network 110, and/or some other network, such as a cellular network. Thus, for example, the wrist device 102 may be connected (i.e. wirelessly connected) to the portable electronic device 106, such as a mobile phone, smart phone, tablet and/or computer to name a few. This may enable data transfer between the wrist device 102 and the portable electronic device 106. The data transfer may be based on Bluetooth protocol, for example. Other wireless communication methods, such as Wireless Local Area Network (WLAN) and/or Near Field Communication (NFC), may also be used.

Figure 2:
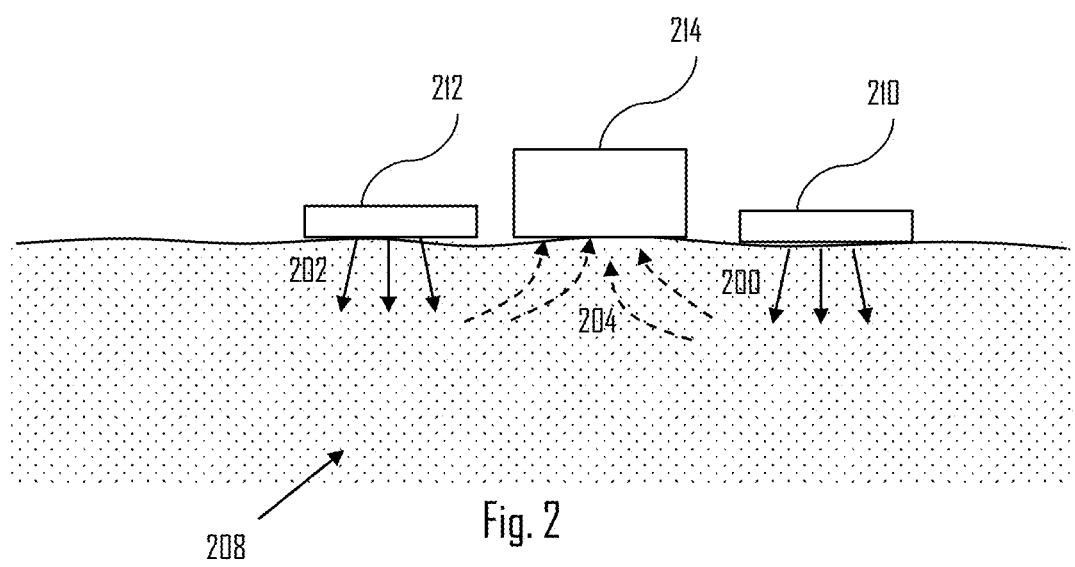
FIG. 2 illustrates a basic principle of optical heart activity measurement.

The wrist device 102 may comprise a heart activity sensor configured to determine cardiac activity of the user 100, such as heart rate, heart beat interval (HBI) and/or heart rate variability (HRV), for example. The heart activity sensor may comprise an optical cardiac activity sensor unit configured to measure the cardiac activity of the user 100 by using optical measurements. An example of such sensor is a PPG (photoplethysmography) sensor. FIG. 2 illustrates a sensor head of a PPG sensor, comprising multiple light emitting diodes (LEDs) 210, 212 and a photo sensor such as a photodiode 214. The optical measurements may comprise the LEDs 210, 212 emitting light 200, 202 towards body tissue 208 of the user 100 and measuring the bounced, reflected, diffracted, scattered and/or emitted light 204 from the body tissue of the user 100 by using the photodiode 214. The emitted light is modulated when travelling through veins of the user 100 and the modulation may be detected by the optical cardiac activity sensor unit. By using detected optical measurement data, the wrist device 102 may determine cardiac activity of the user 100, such as the heart rate. The optical cardiac activity sensor unit may obtain via the measurement a measurement signal characterizing or carrying the cardiac activity information on the user. As understood, similar cardiac activity circuitry may be comprised in the other wearable devices described herein.

It also needs to be noted that the cardiac activity circuitry may produce raw measurement data of the cardiac activity and/or it may process the measurement data into cardiac activity information, such as heart rate for example. The sensor(s) in the cardiac activity circuitry may comprise data processing capabilities. Also, the wrist device 102 and/or some other wearable device may comprise a processing circuitry configured to obtain the cardiac activity measurement data from the cardiac activity circuitry and to process said data into cardiac activity information, such as a cardiac activity metric characterizing the cardiac activity of the user 100. For example, the measurement data of the optical cardiac activity sensor unit may be used, by the processing circuitry, to determine heart rate, HRV and/or HBI of the user 100. Further, the raw measurement data and/or processed information may be processed by the wrist device 102 or some other wearable device, and/or transmitted to an external device, such as the portable electronic device 106.

The wrist device 102 (or more broadly, the wearable device) may comprise other types of sensor(s). Such sensor(s) may include a Laser Doppler-based blood flow sensor, a magnetic blood flow sensor, an Electromechanical Film (EMFi) pulse sensor, a temperature sensor, a pressure sensor, an electrocardiogram (ECG) sensor, and/or a polarization blood flow sensor.

Measuring cardiac activity of the user with the optical cardiac activity sensor unit (referred to simply as OHR), may be affected by motion artefacts. That is, motion artefacts may cause an effect on the measured cardiac activity signal. The effect may cause the information carried by the signal to be erroneous and/or incomplete. Some embodiments described below provide a solution to reduce the effect of motion artefacts on a cardiac activity signal measured using the OHR. The solution may enable the users to receive even more accurate cardiac activity information to help them, for example, during physical training or to plan their future training sessions.

Figure 3:
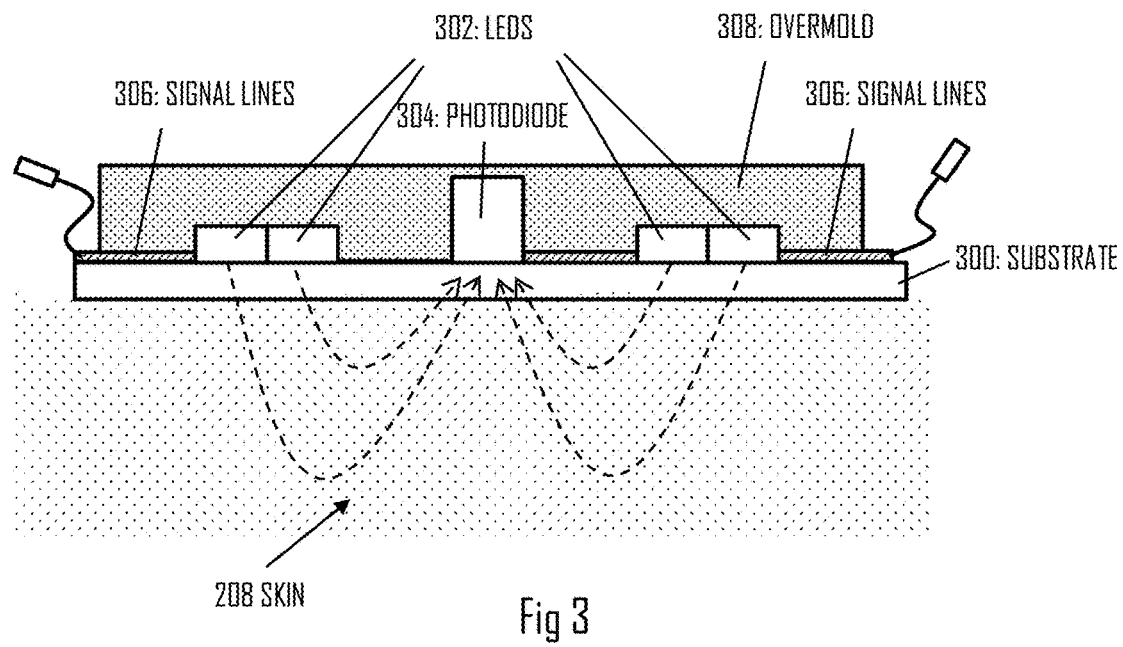
FIG. 3 illustrates a heart activity sensor device according to an embodiment of the invention.

FIG. 3 illustrates an embodiment of a wearable heart activity sensor device comprising: a substrate 300 of optically transparent material arranged to face a skin 208 of a user when the sensor device is worn by the user; at least one LED 302 arranged on the substrate 300 and arranged to emit light through the substrate 300; at least one photo sensor 304 arranged on the substrate 300 as spatially separated from the at least one LED 302 and arranged to absorb light through the substrate, wherein the at least one LED and the at least one photodiode are comprised in a PPG sensor of the heart activity sensor device; and an overmold 308 of thermoplastic material covering the at least one LED 302, the at least one photo sensor 304 and a space between the at least one light emitting diode and the at least one photodiode.

The overmold 308 fills all the spaces between the components assembled on the substrate and, upon solidifying, provides a rigid structure and support for the electronic components. This thermoplastic nature of the overmold 308 also enables a very thin structure for protecting the components of the PPG sensor.

In an embodiment where the overmold is of optically non-transparent thermoplastioc material, the overmold also provides for an optical barrier between the LED(s) and the photo sensor(s) by covering the space(s) therebetween. The optical barrier reduces or eliminates a direct light path from the LED(s) to the photo sensor(s), thus improving the quality of measurements. Accordingly, the overmold may have three functions in a simple construction: the optical barrier, the rigid support for the electronics on the substrate 300, and a cover for the electronics on the substrate 300.

Furthermore, assembling the optoelectronic components of the PPG sensor on the substrate ensures that they are inherently at the same distance from the skin. Moreover, different dimensions of the LED(s) and the photo sensors will not cause negative effects. These factors improve the quality of PPG measurements.

In addition to the electronic components such as the LED(s) and the photo sensor(s) of the PPG sensor head, signal lines 306 coupling to the electronic components may be provided on the substrate 300 before overmolding.

Figure 4:
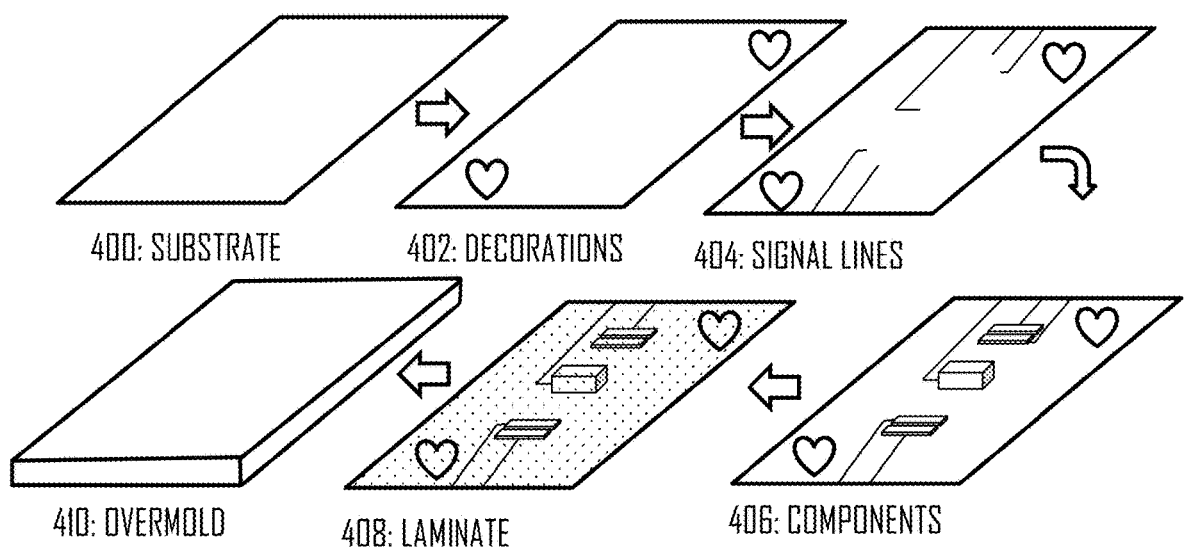
FIG. 4 illustrate manufacturing steps of the heart activity sensor device according to an embodiment of the invention.

Let us next describe a method for manufacturing the wearable heart activity sensor device of FIG. 3. Referring to FIG. 4, the method comprises obtaining 400 a substrate of optically transparent material; assembling 406 at least one LED of a PPG sensor on the substrate such that the at least one LED is arranged to emit light through the substrate; assembling 406 at least one photo sensor of the PPG sensor on the substrate as spatially separated from the at least one LED and such that the at least one photo sensor is arranged to absorb light through the substrate; and overmolding 410 the at least one light emitting diode, the at least one photo sensor and a space between the at least one LED and the at least one photo sensor with thermoplastic material.

The manufacturing process may comprise additional steps also illustrated in FIG. 4. In an embodiment, patterns such as graphics, colours and/or decorations may be provided (402) on the substrate. The patterns may serve for a decorative purpose or have a technical character such as serving as an indicator related to a function of the heart activity sensor. The patterns may be printed on the substrate by using inkjetting, pad printing, digital printing, vacuum metallization, coating, or screen printing.

The signal lines may also be provided (404) on the substrate before the overmolding. The signal lines may be provided by using various techniques, e.g. copper lines, printing and/or application of conductive adhesive and/or conductive ink, flexible printed circuit board(s), or laser direct structuring. Combinations of such techniques may also be employed. For example, some of the signal lines may be printed on the substrate and further signal lines or connections between the signal lines may be added thereafter by applying drops of conductive ink and/or adhesive. As another example, components may be applied to the substrate comprising the signal lines, and the components may be coupled to appropriate signal lines by applying the drops of conductive ink and/or adhesive.

In some embodiments, the substrate comprising the components may be laminated before the overmolding. In particular, when at least some of the components are relatively high or otherwise susceptible to get displaced during the overmolding, the lamination prevents or reduces such an effect.

In an embodiment, the substrate is a film or a foil.

In an embodiment, the substrate is made of plastics or a polymer such as polycarbonate, Polymethyl methacrylate, polyimide, or polyethylene terephthalate (PET). In another embodiment, the substrate is glass.

In an embodiment, thickness of the substrate is 0.76 millimetres or less. In an embodiment, thickness of the substrate is 0.50 millimetres or less. In an embodiment, thickness of the substrate is 0.250 millimetres or less. In an embodiment, thickness of the substrate is 0.175 millimetres or less. In an embodiment, thickness of the substrate is 0.125 millimetres or less. Thinner substrates enable reduction in thickness of the assembly while thicker substrates provide for better support during the overmolding. In an embodiment, thickness of the substrate is between 0.76 and 0.25 millimetres. In an embodiment, thickness of the substrate is at least 0.25 millimetres to facilitate the overmolding.

In an embodiment, the components are glued to the substrate in step 406. One or several types of glues may be employed. For example, one glue may provide the structural attachment to the substrate while another, conductive glue is used to couple each component to one or more signal lines. In another embodiment, a single glue providing both the structural attachment and the electric coupling is used. Yet another glue may be employed to cover the components during the lamination step 408.

In an embodiment, the manufacturing process further comprises providing a hard coating on the side of the substrate that faces the skin 208. The hard coating provides for mechanical protection.

In an embodiment, the manufacturing method is performed by using in-mold labelling (IML) technology.

In an embodiment, the manufacturing method is performed by using injection molding decoration (IMD) technology also called in-mold-decoration.

In an embodiment, the manufacturing method is performed by using film insert molding (FIM) technology.

In an embodiment, the manufacturing method is performed by using injection molded structural electronics (IMSE®) technology.

In an embodiment, the overmold of thermoplastic material may is thermoplastic polyurethane or other thermoplastic elastomer.

In an embodiment, the manufacturing process of FIG. 4 further comprises a step of thermoforming the substrate. Thermoforming may be used to shape the substrate to have a desired form. For example, the substrate may be curved by using the thermoforming. The thermoforming may be carried out before assembling the components in step 406. In this manner, the thermoforming will not cause displacement of the components and disconnection of the components from the signal lines. The thermoforming may be carried out between steps 400 and 402 or between steps 404 and 406, for example. In another embodiment, the thermoforming is performed after assembling the components, i.e. after step 406.

Figure 5:
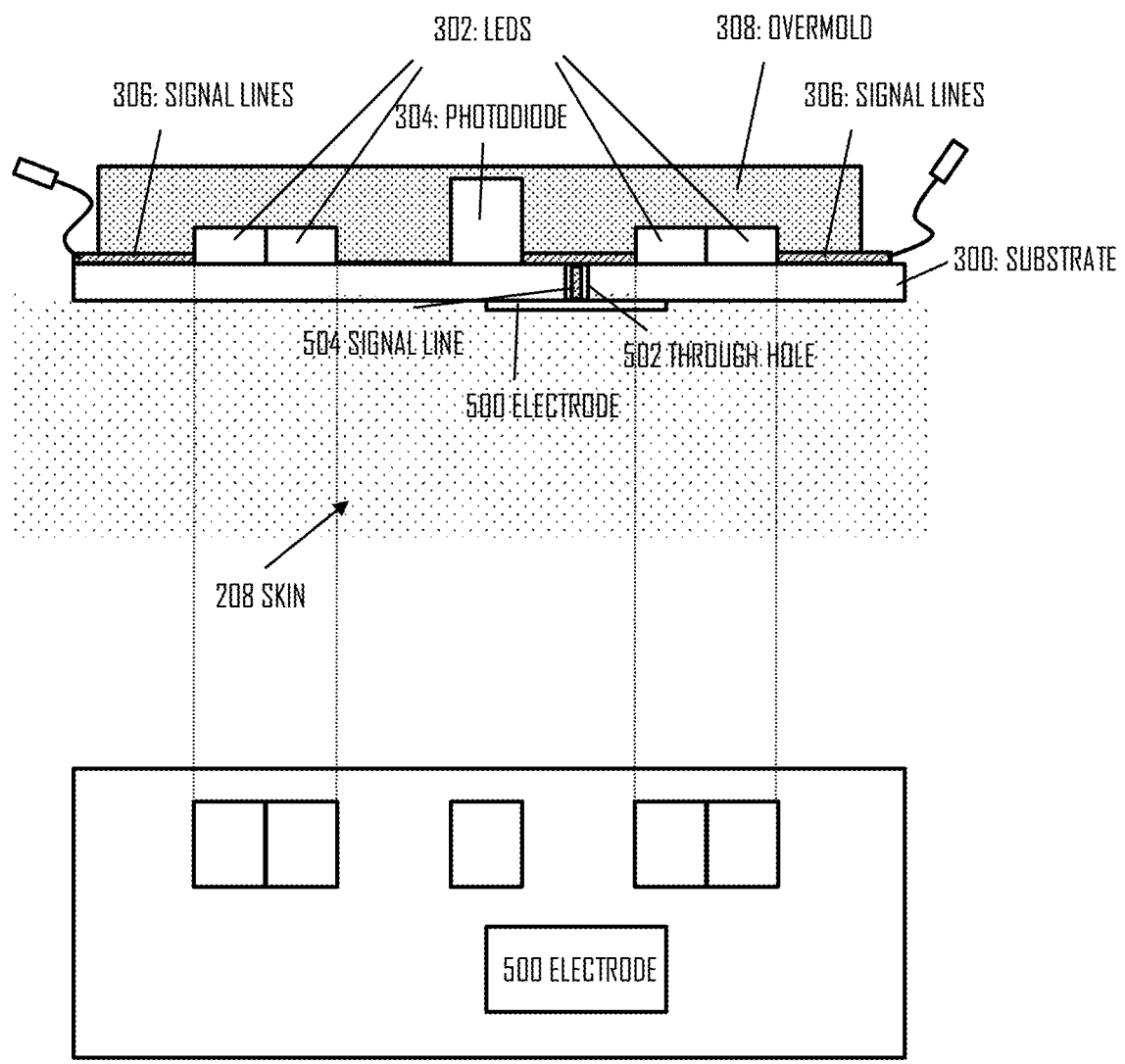
FIG. 5 illustrates a heart activity sensor device according to another embodiment of the invention.

In an embodiment, the heart activity sensor device further comprises at least one skin measurement electrode arranged on the substrate on the opposite side than the at least one LED and the at least one photo sensor, i.e. on the side facing the skin 208. FIG. 5 illustrates such an embodiment. The skin measurement electrode 500 may be an electrode for an ECG sensor, bioimpedance sensor, or a skin temperature sensor. The skin measurement electrode may be assembled on the substrate in step 406. FIG. 5 illustrates the assembly comprising the electronic components on the substrate from two viewpoints to illustrate the layers of the assembly and placement of the electronic components on the substrate. In the lower part, it can be seen that the skin measurement electrode(s) 500 may be arranged in the layout such that PPG measurements are not degraded. The optical barrier formed by the overmold 308 may still be provided between the LED(s) and the photo sensor(s).

In an embodiment, the substrate 300 comprises at least one through hole 502 for a signal line 504 to the at least one skin measurement electrode 500. The through hole may be formed before step 404, and the signal line through the through hole may be formed in step 404. The signal line 504 may substantially fill the through hole, or the signal line may be formed on the edges of the through hole from one side of the substrate to the other side via the through hole. Thereafter, the through hole 502 may be filled to make it 502 waterproof. The filling waterproofness may be realized by mechanical pressure by using a gasket or a similar element. In another embodiment, the hole may be filled with elastomer, adhesive, or similar material that fills the hole in a waterproof manner.

In an embodiment, the substrate 300 comprises multiple through holes for signal lines to multiple skin electrodes, wherein one skin electrode may be a ground electrode and another skin electrode may be a measurement electrode. Multiple measurement electrodes and corresponding through holes may be provided, e.g. for measuring bioimpedance.

In the embodiments where substrate that comprises the PPG measurement head and the electrodes, the wearable device may be configured to carry out various measurements. The various measurements may be carried out in different operational modes. One measurement mode may employ only the electrode(s), and the PPG measurement head may be disabled. In such a measurement mode, the electrodes may be used for measuring bioimpedance and/or electrocardiogram. In another measurement mode, the electrode(s) may be disabled, and the PPG measurement head may be enabled to measure heart activity and/or oxygen saturation. In yet another measurement mode, both the electrode(s) and the PPG measurement head may be enabled to perform measurements, e.g. to measure a pulse transit time or blood pressure. In this measurement mode, both the PPG measurements and the electrodes may be used to measure the pulse transit time or blood pressure. For example, the electrodes may be used to compute electrocardiogram that indicates a timing of a blood pulse at a heart, and the PPG measurement head may be used to detect the blood pulse at another location in the user's body, e.g. the wrist. A time difference between the electrocardiogram detection of the blood pulse and the PPG detection of the blood pulse represents the pulse transit time that may be used for computing the blood pressure, for example.

In an embodiment, the LED(s) and the photo sensor(s) of the PPG sensor head are provided in a strap of a wrist-worn heart activity sensor device. The LED(s) and the photo sensor(s) of the PPG sensor may be provided at a location of a casing housing other electronics of the wrist device, e.g. a display screen. In another embodiment, The LED(s) and the photo sensor(s) of the PPG sensor may be provided at a location offset from the location of the casing, e.g. the PPG sensor head may be provided such that it will be disposed at an opposite side of the wrist than the display screen, when the user wears the wrist device.

Figure 6:
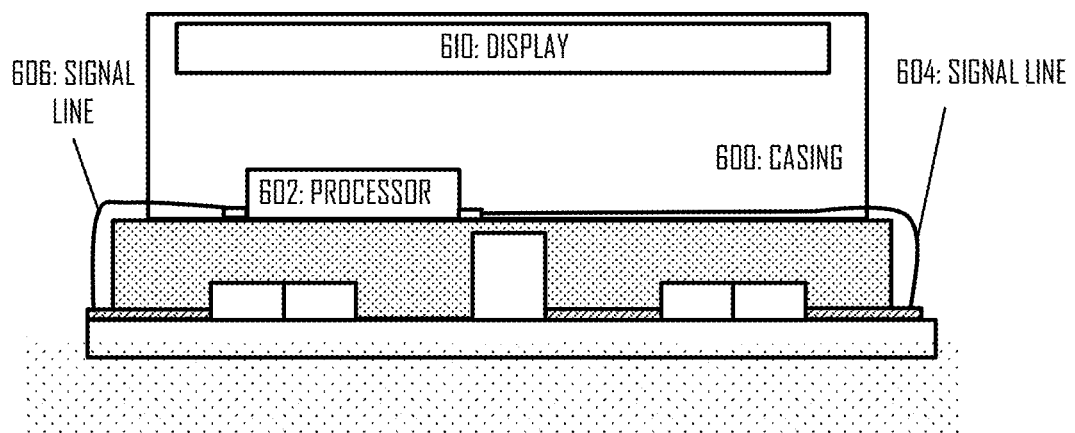
FIGS. 6 and 7 illustrate further embodiments of the heart activity sensor device.

In an embodiment, the wearable heart activity sensor device further comprises at least one processor external to the overmold of thermoplastic material; and signal lines arranged on the substrate inside and outside the overmold to couple the at least one processor to the at least one light emitting diode and the at least one photo sensor. FIG. 6 illustrates such an embodiment.

As already illustrated in FIGS. 3 and 5, the overmold 308 may cover the signal lines 306 only partially and leave a part of the signal lines exposed such that the signal lines 306 may be coupled to electronics external to the overmold. Referring to FIG. 6, the processor(s) 602 may be provided in a casing 600 assembled on the overmold. The casing may further comprise the display screen 610. Signal lines disposed on the substrate may be coupled to the processor(s) 602 by further signal lines 604, 606 that may comprise cables and, optionally, suitable connector(s). In an embodiment, the signal lines 604, 606 are provided through one or more through holes in the overmold and through the bottom of the casing 600 such that the casing protects the signal lines 604, 606.

Figure 7:
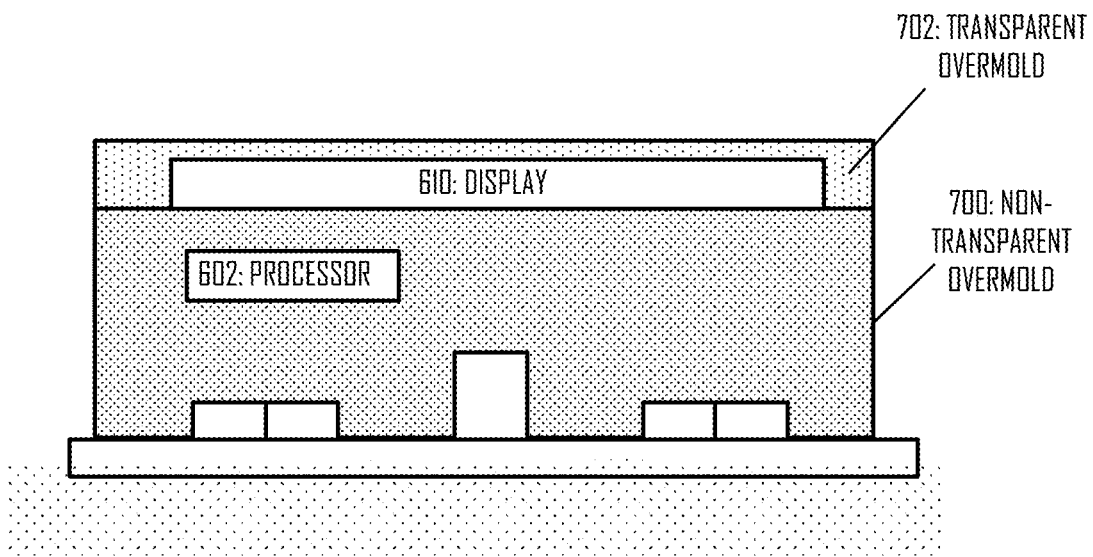

In the embodiment of FIG. 6, the processor and the display screen are external to the overmold. In the embodiment of FIG. 7, the processor and the display are comprised in the over mold. The processor and, optionally, other integrated circuits may be assembled on the substrate in step 406, and the overmold 308 may cover the processor and the integrated circuits. Even the display screen may be assembled on the substrate and covered by the overmold, e.g. in the embodiments where the overmold is optically transparent. In embodiment where the overmold is optically non-transparent, the display screen 610 may be assembled on top of the non-transparent overmold 700, and a transparent overmold layer 702 of thermoplastic material may be provided to cover the display screen.

Figure 8:
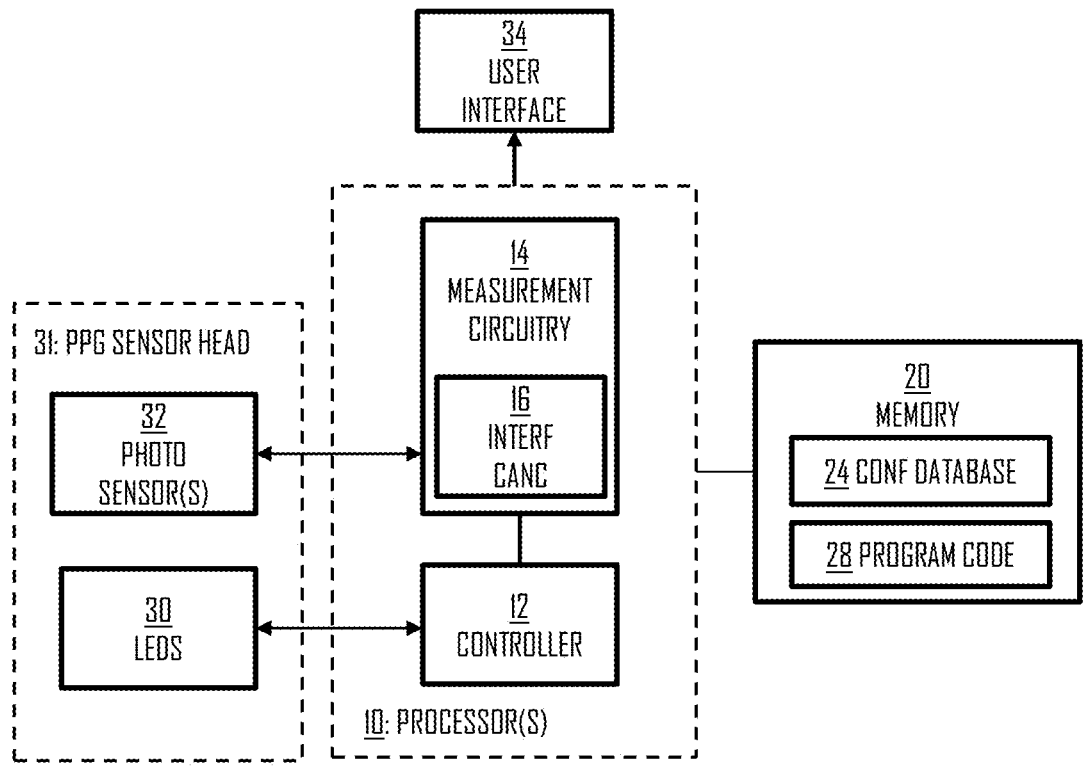
FIG. 8 illustrates a block diagram of an apparatus according to an embodiment of the invention.

Let us then describe an embodiment addressing the problem of motion artefacts mentioned above. Referring to FIG. 8, a wearable sensor device comprises: a PPG sensor head 31 comprising a first set of LEDs 30 arranged to emit light at a first wavelength and a second set of LEDs 30 arranged to emit light at a first wavelength different from the first wavelength, wherein the first set of LEDs and second set of LEDs are arranged spatially in pairs such that each pair of LEDs comprises a LED of the first set and a LED of the second set disposed directly next to one another, and wherein different pairs of LEDs are spatially separated from one another, the PPG sensor head further comprising at least one photo sensor 32; a controller 12 configured to activate the LEDs 30 to emit light in a sequential manner such that LEDs of each pair are activated at different timings; a measurement circuitry 14 configured to acquire a first measurement signal from the at least one photo sensor when a first LED of a pair of LEDs is emitting light and further configured to acquire a second measurement signal from the at least one photo sensor when a second LED of the pair of LEDs is emitting light, to remove motion interference from at least one of the first measurement signal and the second measurement signal by using common mode interference cancellation on the first measurement signal and the second measurement signal. The interference cancellation may be performed by an interference cancellation circuitry 16.

The arrangement of the LEDs spatially in pairs provides for a technical effect that a source location (LED) and a sink location (photo sensor) of a light path for measurements remain are the same for the first measurement signal and the second measurement signal. The arrangement of the LEDs in pairs such that each pair comprises a LED of each wavelength provides the technical effect that they travel a different path from the source to the sink in the tissue/skin. For example, green light penetrates the tissue deeper than red light. Other wavelengths may naturally be employed in the LEDs. The different paths cause the effect that the first measurement signal will differ from the second measurement signal and, further, that the motion artefacts are induced to the first measurement signal and the second measurement signal with the same characteristics. Since the interference signal is substantially similar in the first measurement signal and the second measurement signal, i.e. common mode interference, the common mode interference cancellation is able to cancel the interference from the measurement signals. The interference cancellation may be performed on either the first measurement signal or the second measurement signal. Advantageously, the interference cancellation is performed on the signal more suitable for the main purpose, e.g. if the purpose is heart rate measurement, the measurement signal measured from green light would be preferred over a measurement signal measured from red light, for example.

When applied to any one of the embodiments of FIGS. 3 to 7, the overmold may cover a space or spaces between the different pairs of LEDs. Since LEDs of a pair are directly next to one another, the overmold may not extend between the LEDs of the pair.

In a very simple embodiment, the common mode interference cancellation cancels the common mode interference by subtracting samples of the first measurement signal from samples of the second measurement signal, thus negating the common mode interference. More sophisticated common mode interference cancellation may, however, be used.

The controller may also control the measurement circuitry to measure a measurement signal from selected one or more photo sensors according to the sequence in which the LEDs are activated, as described in greater detail below with reference to Tables.

The controller and the measurement circuitry may be comprised in the at least one above-described processor 602 or processing circuitry. The wearable sensor device may be any one of the above-described devices, e.g. the wrist device. The sensor device may further comprise a communication interface providing the sensor device with wireless communication capability according to a radio communication protocol. The communication interface may support Bluetooth® protocol, for example Bluetooth Low Energy or Bluetooth Smart.

The training computer may further comprise a user interface 34 comprising the display screen and input means such as buttons or a touch-sensitive display. The processor(s) 10 may output the instructions regarding the exercise to the user interface 34, e.g. on the basis of PPG measurements performed by the measurement circuitry 14.

The sensor device may further comprise or have access to at least one memory 20. The memory 20 may store a computer program code 24 comprising instructions readable and executable by the processor(s) 10 and configuring the above-described operation of the processor(s). The memory 20 may further store a configuration database 28 defining parameters for the processing circuitry, e.g. the sequence for the LEDs used by the controller 12.

As used in this application, the term 'circuitry' refers to all of the following: (a) hardware-only circuit implementations, such as implementations in only analog and/or digital circuitry, and (b) combinations of circuits and software (and/or firmware), such as (as applicable): (i) a combination of processor(s) or (ii) portions of processor(s)/software including digital signal processor(s), software, and memory(ies) that work together to cause an apparatus to perform various functions, and (c) circuits, such as a microprocessor(s) or a portion of a microprocessor(s), that require software or firmware for operation, even if the software or firmware is not physically present. This definition of 'circuitry' applies to all uses of this term in this application. As a further example, as used in this application, the term 'circuitry' would also cover an implementation of merely a processor (or multiple processors) or a portion of a processor and its (or their) accompanying software and/or firmware.

The techniques and methods described herein may be implemented by various means. For example, these techniques may be implemented in hardware (one or more devices), firmware (one or more devices), software (one or more modules), or combinations thereof. For a hardware implementation, the apparatus(es) of embodiments may be implemented within one or more application-specific integrated circuits (ASICs), digital signal processors (DSPs), digital signal processing devices (DSPDs), programmable logic devices (PLDs), field programmable gate arrays (FPGAs), graphics processing units (GPUs), processors, controllers, micro-controllers, microprocessors, other electronic units designed to perform the functions described herein, or a combination thereof. For firmware or software, the implementation can be carried out through modules of at least one chipset (e.g. procedures, functions, and so on) that perform the functions described herein. The software codes may be stored in a memory unit and executed by processors. The memory unit may be implemented within the processor or externally to the processor. In the latter case, it can be communicatively coupled to the processor via various means, as is known in the art. Additionally, the components of the systems described herein may be rearranged and/or complemented by additional components in order to facilitate the achievements of the various aspects, etc., described with regard thereto, and they are not limited to the precise configurations set forth in the given figures, as will be appreciated by one skilled in the art.

FIGS. 9 to 14 illustrate different layouts of the PPG sensor head 31. The layouts comprise multiple pairs of LEDs and most of the embodiments comprise multiple photo sensor to provide multiple, mutually orthogonal spatial measurement channels to improve the accuracy of the measurements. A purpose in some of the described embodiments that use multiple measurement channels is that a distance the light travels from a LED to the photo diode remains substantially constant in the multiple measurement channels. As a consequence, a measurement configuration employing the multiple spatial measurement channels comprises a first pair of LEDs and a second pair of LEDs that are substantially at the same distance from a photo sensor sensing light from the first and second pairs of LEDs.

Figure 9:
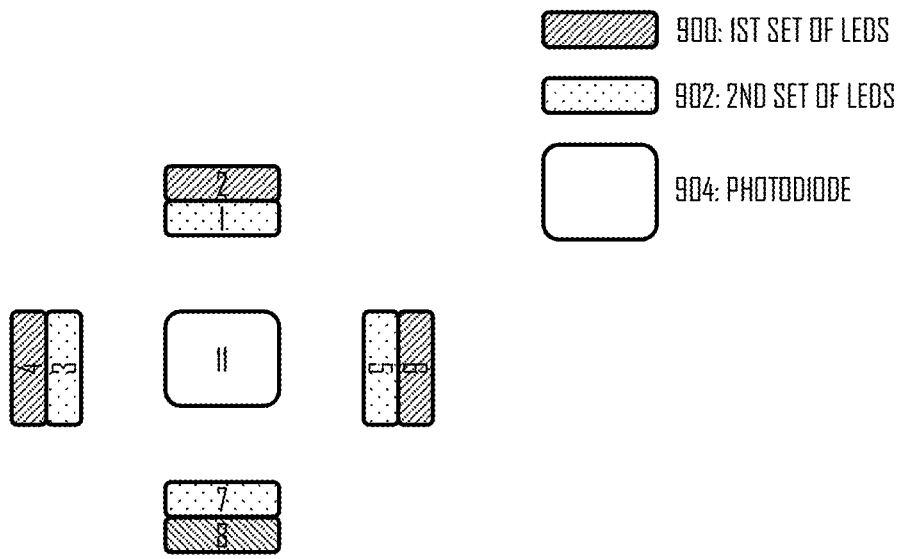
FIG. 9 illustrates an arrangement of a photoplethysmogram (PPG) sensor head according to an embodiment of the invention.

FIG. 9 illustrates a first embodiment of the layout. The pairs of LEDs are disposed to different directions from the photo sensor 904, e.g. along an imaginary annulus around the photo sensor where the photo sensor is at an origin of the annulus. In the embodiment of FIG. 9, the four pairs of LEDs form a cross with the photo sensor. Referring to FIG. 9, the filling pattern distinguishes the different sets of LEDs. LEDs having diagonal line filling belong to the first set of LEDs 900 while dotted filling refers to the second set of LEDs 902.

The numbers in FIG. 9 inside the LEDs and the photo sensor refer to the sequence in which the LEDs are lighted by the controller. Table 1 below illustrates an embodiment of a sequence for the layout of FIG. 9

TABLE 1

| Measurement index | Activated Photo Sensor | Activated LED |
| --- | --- | --- |
| 1 | 11 | 1 |
| 2 | 11 | 2 |
| 3 | 11 | 3 |
| 4 | 11 | 4 |
| 5 | 11 | 5 |
| 6 | 11 | 6 |
| 7 | 11 | 7 |
| 8 | 11 | 8 |

As can be seen from Table 1, the controller may be configured to activate the LEDs such that LEDs of the same pair of LEDs are activated one directly after the other. This provides for that the first measurement signal and the second measurement signal are measured substantially under the same conditions regarding the motion artefacts.

A measurement channel may be understood as the path from one LED to one photo sensor. Accordingly, LEDs of each pair provide for substantially identical measurement channels towards a photo sensor, e.g. the photo sensor 11. Each LED may emit light for a determined time interval as controlled by the controller 12. In an embodiment, the time interval is between 1 and 100 microseconds (us). During that time, the measurement circuitry may sample an electric output of the photo sensor and acquire digital measurement signals.

Moreover, the LEDs are disposed such that each LED of the first set of LEDs 900 is disposed at an equal distance from the photo sensor 11 and, similarly, each LED of the second set of LEDs 902 is disposed at an equal distance from the photo sensor 11. In the embodiment of FIG. 9, the first set of LEDs 900 forms an outer ring around the photo sensor 11, while the second set of LEDs 902 forms an inner ring around the photo sensor 11. Since the dimensions of the LEDs are non-zero, such an arrangement may be used to improve the accuracy when combining the multiple measurement channels in the measurement circuitry 14. Combining the measurements carried out by using multiple spatial channels improves the accuracy of the heart activity measurements.

Figure 10:
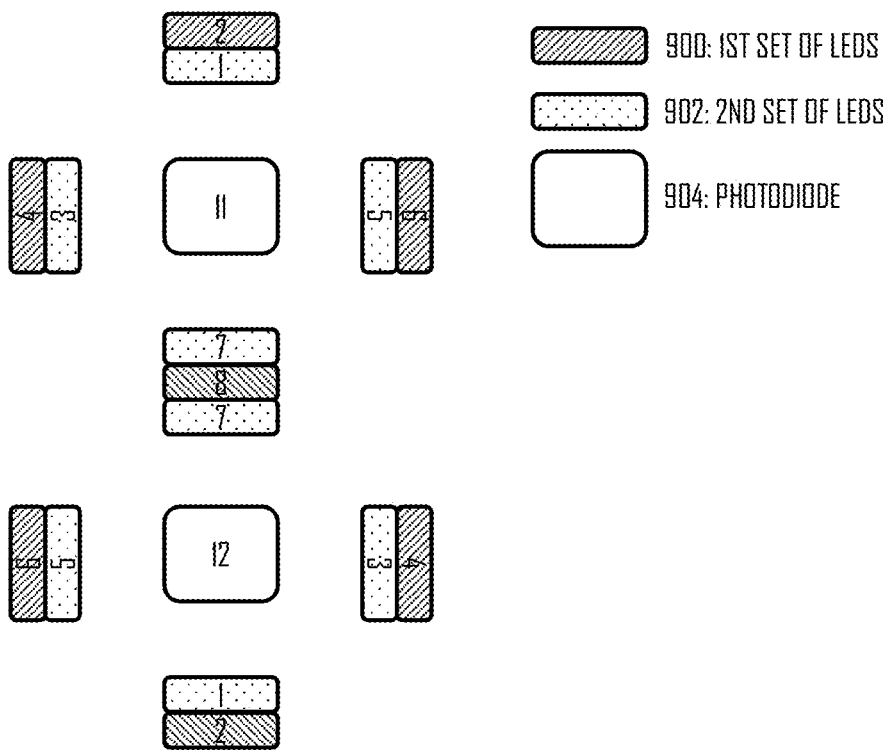
FIGS. 10 and 11 illustrate embodiments of a PPG sensor head comprising multiple photo sensors and multiple pairs of light emitting diodes (LEDs)

FIG. 10 illustrates another embodiment which is an extension of the layout of FIG. 9. In the embodiment of FIG. 10, two photo sensors 11 and 12 are provided, and the pairs of LEDs are disposed in two groups: one group around the photo sensor 11, as described above with reference to FIG. 9, and another group around the photo sensor 12. The other group comprises multiple pairs of LEDs is disposed around a second photo sensor 12 such that LEDs of the first set of LEDs 900 in the second group are disposed at an equal distance from the second photo sensor 12 and LEDs of the second set of LEDs 902 in the second group are disposed at an equal distance from the second photo sensor 12. LED 8 belongs to both sets. The three LEDs disposed denoted by numbers 7 and 8 between the first photo sensor 11 and the second photo sensor 11 form two pairs of LEDs: an upper LED denoted by 7 forms a first pair with LED 8 and forms a measurement channel towards the photo diode 11, while a lower LED denoted by 7 forms a second pair with LED 8 and forms a measurement channel towards the photo diode 12. Table 2 below illustrates an embodiment of a sequence for lighting the LEDs in the layout of FIG. 10.

TABLE 2

| Measurement index | Activated Photo Sensor | Activated LED |
| --- | --- | --- |
| 1 | 11 | 1 |
| 2 | 11 | 2 |
| 3 | 12 | 1 |
| 4 | 12 | 2 |
| 5 | 11 | 3 |
| 6 | 11 | 4 |
| 7 | 12 | 3 |
| 8 | 12 | 4 |
| 9 | 11 | 5 |
| 10 | 11 | 6 |
| 11 | 12 | 5 |
| 12 | 12 | 6 |
| 13 | 11 | 7 |
| 14 | 11 | 8 |
| 15 | 12 | 7 |
| 16 | 12 | 8 |

The sequence of Table 2 enables simultaneous measurements by both (all) photo sensors 11, 12. For example, LEDs denoted by number 1 are so distant from one another that light emitted by them reaches only the closest photo sensor. Some light may reach the more distant photo sensor but it would have such a low intensity with respect to the light from the closer LED that it would cause little interference to the measurements.

In another embodiment, when only one of the photo sensors is configured to measure at a time, only the LED closest to the measuring photo sensor is activated amongst the LEDs having the same number in FIG. 10. For example, when the measurement index 1 is selected, only the LED having the reference number 1 and being closest to the photo sensor 11 is enabled to emit light, and the other LED 1 distant to the photo sensor 11 is disabled. The same applies to the other measurement indices. This embodiment applies to the other embodiments described below in a straightforward manner.

In an embodiment that is a modification of FIG. 10, LEDs denoted by numbers 3, 4, 5 and 6 are omitted. Table 2 may be modified accordingly by removing respective lines from the Table.

Figure 11:
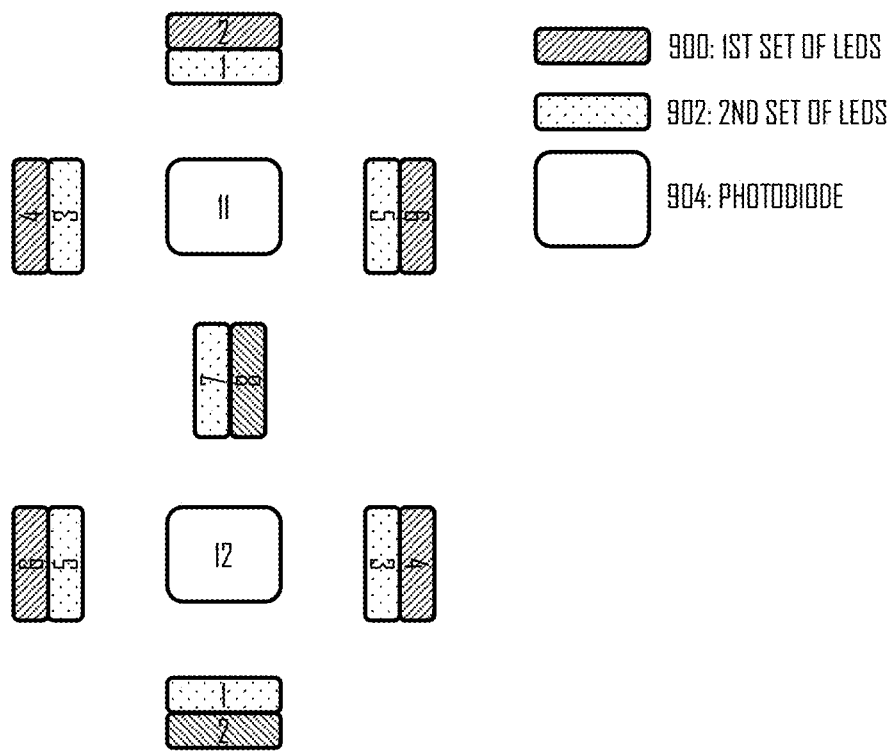

FIG. 11 illustrates a further modification of the embodiment of FIG. 10. In this embodiment, the LEDs 7, 8 between the photo sensors are rotated by 90 degrees with respect to the embodiment of FIG. 10 and one of the LEDs of the second set of LEDs 902 denoted by number 7 is omitted. This reduces the number of structural elements by one LED. However, the distance from the LEDs 7, 8 to the photo sensor 11 or 12 may differ slightly from the distance between the photo sensors 11, 12 and the other LEDs 1, 2, 3, 4, 5, 6. The sequence of Table 2 may still be used.

Figure 12:
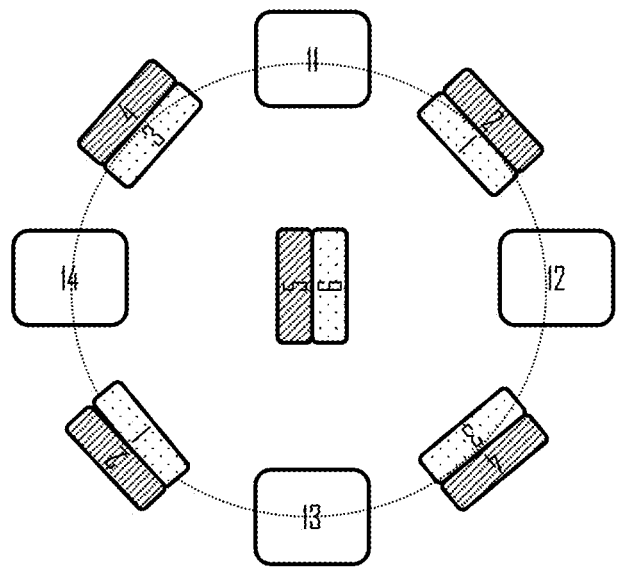
FIGS. 12 to 14 illustrate embodiments where photo sensors and LEDs are arranged along one or more annuli.
Figure 13:
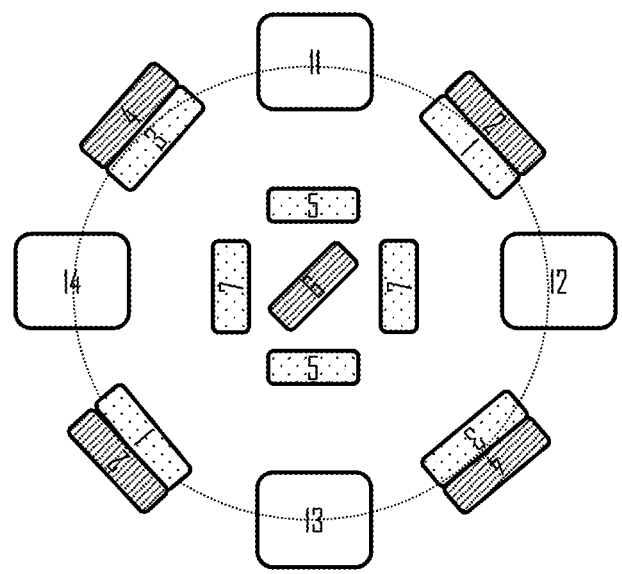

FIGS. 12 and 13 illustrate embodiments where the pairs of LEDs and the photo sensors are arranged along an imaginary annulus (illustrates by a dotted annulus) in an alternating manner that each pair of the pairs of LEDs is between two photo sensors and each photo sensor is between two pairs of LEDs along the annulus. Furthermore, at least one pair of LEDs is provided at a centre of the imaginary annulus. In the embodiment of FIG. 12 just like in the embodiments of FIGS. 10 and 11, the measurement channels are formed between a LED pair and the closest photo sensor(s). This may be arranged by designing the spatial distribution of the LEDs and the photo sensors appropriately. Light from a LED distant to a photo sensor will not substantially reach the photo sensor. The required distance will be decided by illumination intensity of the LED with respect to the distance between the photo sensor and the LED.

The embodiment of FIG. 12 comprises the pair of LEDs 5, 6 at the centre of the annulus. With respect to the other pairs of LEDs disposed along the annulus, the first set of LEDs forms an inner ring and the second set of LEDs forms an outer ring, thus providing substantially equal distances to the photo sensors. The LEDs 5, 6, at the centre deviate from this symmetricity to some degree but the advantage is reduced number of components (LEDs). Table 3 below illustrates an embodiment of a sequence for lighting the LEDs in the layout of FIG. 12.

TABLE 3

| Measurement index | Activated Photo Sensor | Activated LED |
|---|---|---|
| 1 | 11 | 1 |
| 2 | 11 | 2 |
| 3 | 13 | 1 |
| 4 | 13 | 2 |
| 5 | 11 | 3 |
| 6 | 11 | 4 |
| 7 | 13 | 3 |
| 8 | 13 | 4 |
| 9 | 12 | 1 |
| 10 | 12 | 2 |
| 11 | 14 | 1 |
| 12 | 14 | 2 |
| 13 | 12 | 3 |
| 14 | 12 | 4 |
| 15 | 14 | 3 |
| 16 | 14 | 4 |
| 17 | 11 | 5 |
| 18 | 11 | 6 |
| 19 | 12 | 5 |
| 20 | 12 | 6 |
| 21 | 13 | 5 |
| 22 | 13 | 6 |

TABLE 3-continued

| Measurement index | Activated Photo Sensor | Activated LED |
|---|---|---|
| 23 | 14 | 5 |
| 24 | 14 | 6 |

In the embodiment of FIG. 12 and Table 3, the photo sensor 11 may measure measurement signals from LEDs 1 and 2 next to the photo sensor 11 on the annulus (measurement indices 1 and 2) and perform the common mode interference cancellation on these measurement signals, thus acquiring an interference-cancelled measurement signal. Simultaneously, the measurement indices 3 and 4 may be performed, i.e. the photo sensor 13 may measure measurement signals from LEDs 1 and 2 next to the photo sensor 13 on the annulus and perform the common mode interference cancellation on these measurement signals, thus acquiring an interference-cancelled measurement signal. In the next phase, the photo sensor 11 may measure measurement signals from LEDs 3 and 4 next to the photo sensor 11 on the annulus (measurement indices 5 and 6) and perform the common mode interference cancellation on these measurement signals, thus acquiring another interference-cancelled measurement signal. Simultaneously, the photo sensor 13 may measure the light from LEDs 3, 4 next to the photo sensor 13 in the same manner. Next, the procedure is repeated for the photo sensors 12 and 14 that measure the LEDs 1, 2, 3, and 4 closest to them in the same manner. Then, measurement indices 17, 19, 21, and 23 may be performed simultaneously, i.e. each photo sensor may measure the light from the LED 5 at the centre simultaneously. Thereafter, measurement indices 18, 20, 22, and 24 may be performed simultaneously, i.e. each photo sensor may measure the light from the LED 6 at the centre simultaneously and perform the interference cancellation on the measurement signals received from the LEDs 5 and 6. As a result, three interference-cancelled measurement signals are available per photo sensor 11 to 14. These measurement signals may then be combined in a desired manner, e.g. only measurement signals measured by the same photo sensor may be combined or even all these measurement signals may be combined for the final computation of the heart activity. In principle, all measurement signals associated with the same set of LEDs 900, 902 may be combined. However, in some cases it may be advantageous to combine only a subset of the measurement signals, e.g. measurement signals associated with LEDs having the same index in the Figures. The LEDs having the same index are disposed on opposite edges of the layout and, thus, at least one of the LEDs can be assumed to have a proper contact with the skin even under rapid motion.

In the embodiment of FIG. 13, further LEDs are provided at the centre to provide the symmetricity with the pairs of LEDs along the annulus. In this embodiment, a LED 6 of the first set of LEDs 900 is provided at the very centre of the annulus, and a number of LEDs of the second set of LEDs 902 is provided around the LED 6. The number of LEDs of the second set of LEDs 902 at the centre and around the LED 6 may equal to the number of photo sensors 11 to 14 in the configuration. The distance to the closest photo sensor from each LED of the second set of LEDs 902 at the centre and around the LED 6 may equal to the distance from the LED(s) of the second set on the annulus to the closest photo sensor, thus providing alike distances between the LEDs having their emitted light measured by the same photo sensor. At the centre of the annulus, each LED 7 of the second set of LEDs 902 forms a pair of LEDs with the LED 6 of the first set of LEDs 900. Table 4 below illustrates an embodiment of a sequence for lighting the LEDs in the layout of FIG. 13.

TABLE 4

| Measurement index | Activated Photo Sensor | Activated LED |
|---|---|---|
| 1 | 11 | 1 |
| 2 | 11 | 2 |
| 3 | 13 | 1 |
| 4 | 13 | 2 |
| 5 | 11 | 3 |
| 6 | 11 | 4 |
| 7 | 13 | 3 |
| 8 | 13 | 4 |
| 9 | 12 | 1 |
| 10 | 12 | 2 |
| 11 | 14 | 1 |
| 12 | 14 | 2 |
| 13 | 12 | 3 |
| 14 | 12 | 4 |
| 15 | 14 | 3 |
| 16 | 14 | 4 |
| 17 | 11 | 5 |
| 18 | 11 | 6 |
| 19 | 13 | 5 |
| 20 | 13 | 6 |
| 21 | 12 | 7 |
| 22 | 12 | 6 |
| 23 | 14 | 7 |
| 24 | 14 | 6 |

In the embodiment of FIG. 13 using the sequence of Table 4, photo sensors 11 and 13 may measure simultaneously as may photo sensors 12 and 14. Accordingly, the following measurement indices may be performed simultaneously: {1, 3}; {2, 4}; {5, 7}; {6, 8}; {9, 11}; {10, 12}; {13, 15}; {14, 16}; {17, 19}; {18, 20}; {21, 23}; {22, 24}.

This embodiment follows mainly the same principles for acquiring the measurement signals as described above with respect to the embodiment of FIG. 12. Regarding the LEDs at the centre, the photo diodes 11 to 14 acquire measurement signals from the LED 6 and the closest one of LEDs 5 or 7 for the interference cancellation. The photo sensors 11 and 13 do not measure light from LEDs 7, for instance. Similarly, the photo sensors 12 and 14 do not measure light from LEDs 5.

Figure 14:
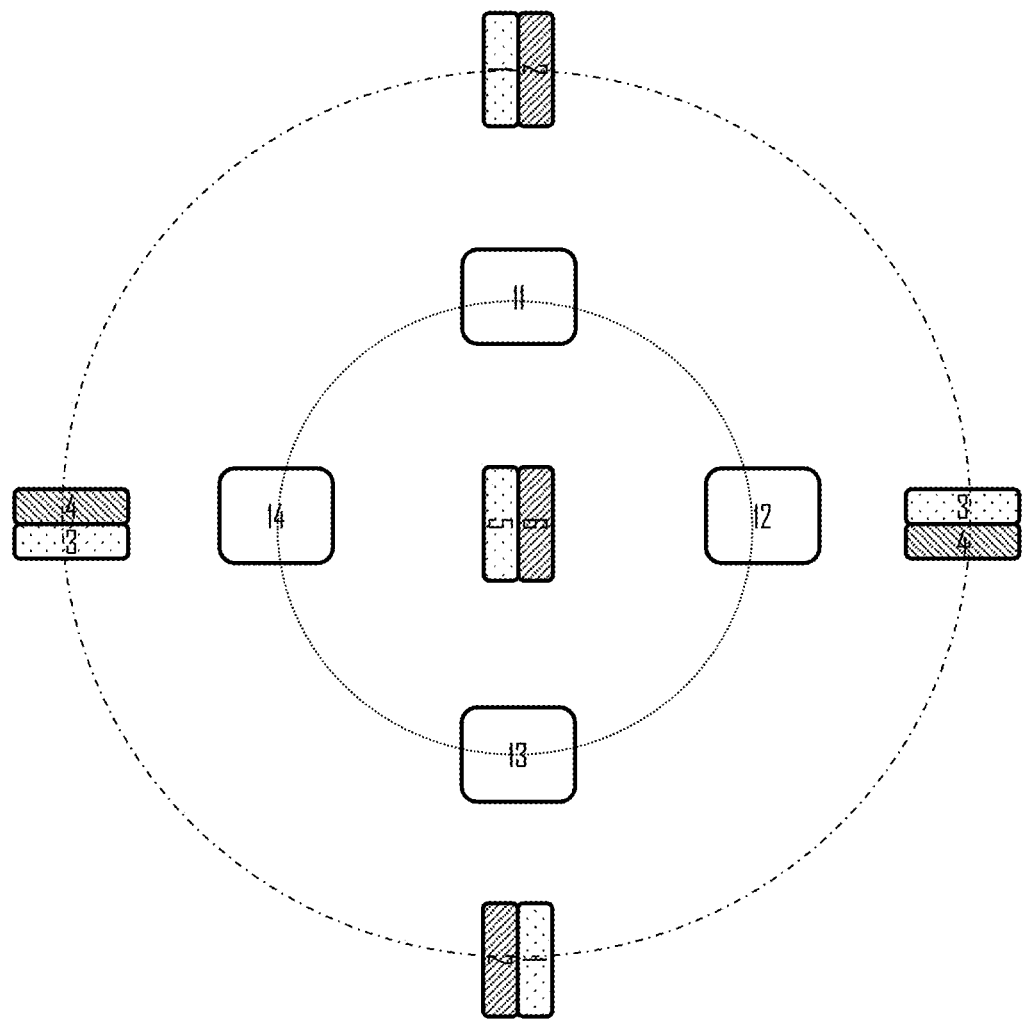

FIG. 14 illustrates yet another embodiment where only the photo sensors are provided along the same annulus, and the LEDs are provided along another annulus, one that has a greater radius (illustrated by dash-dotted line in FIG. 14. A further pair of LEDs is provided at the centres of the annuli. The LEDs on the other annulus are provided at the same locations on the annulus as the photo sensors 11 to 14 on their annulus, i.e. at directions 12 o'clock, 3 o'clock, 6 o'clock, and 9 o'clock. Accordingly, both LEDs 1 to 4 and the photo sensors 11 to 14 are disposed symmetrically on the annuli, e.g. at equal distances. Table 5 below illustrates an embodiment of a sequence for lighting the LEDs in the layout of FIG. 14.

TABLE 5

| Measurement index | Activated Photo Sensor | Activated LED |
|---|---|---|
| 1 | 11 | 1 |
| 2 | 11 | 2 |
| 3 | 13 | 1 |
| 4 | 13 | 2 |
| 5 | 12 | 3 |
| 6 | 12 | 4 |
| 7 | 14 | 3 |
| 8 | 14 | 4 |
| 9 | 11 | 5 |
| 10 | 11 | 6 |
| 11 | 12 | 5 |
| 12 | 12 | 6 |
| 13 | 13 | 5 |
| 14 | 13 | 6 |
| 15 | 14 | 5 |
| 16 | 14 | 6 |

As in the embodiments above, photo sensors 11 and 13 may measure simultaneously, as may photo sensors 12 and 14. Accordingly, corresponding measurement indices of Table 5 may be performed simultaneously.

In the embodiments described above, the LEDs of the same pair are activated one directly after the other, thus providing for substantially identical measurement conditions for the interference cancellation. Such near-simultaneous activation is, however, not necessary. There may be arbitrary delay between the activation of the LEDs of the same pair. In such an embodiment, the measurement circuitry is configured to perform, before the common mode interference cancellation, a time-shift on samples of one of the measurement signals to compensate for the delay in emission times of the LEDs of the same pair of LEDs.

It will be obvious to a person skilled in the art that, as the technology advances, the inventive concept can be implemented in various ways. The invention and its embodiments are not limited to the examples described above but may vary within the scope of the claims.

What is claimed is:

1. A wearable heart activity sensor device comprising:
a substrate of optically transparent material arranged to face a skin of a user when the sensor device is worn by the user;
at least one light emitting diode (LED) arranged on the substrate and arranged to emit light through the substrate, wherein the at least one LED comprises a first set of LEDs arranged to emit light at a first wavelength and a second set of LEDs arranged to emit light at a second wavelength different from the first wavelength, and wherein the first set and second set of LEDs are arranged spatially in pairs such that each pair comprises an LED of the first set and an LED of the second set disposed directly next to one another on the substrate, wherein different pairs of LEDs are spatially separated on the substrate;
at least one photo sensor arranged on the substrate as spatially separated from the at least one LED and arranged to absorb light through the substrate, wherein the at least one LED and the at least one photo sensor are comprised in a photoplethysmogram sensor of the heart activity sensor device, and wherein the at least one photo sensor comprises a plurality of photo sensors, and wherein at least one pair of LEDs is disposed between the plurality of photo sensors, and wherein at least two pairs of LEDs are disposed between opposite sides of one of the plurality of photo sensors; and
an overmold of thermoplastic material covering the at least one light emitting diode, the at least one photo sensor, a space between the at least one light emitting diode and the at least one photo sensor, and a space between the different pairs of LEDs, wherein the overmold of thermoplastic material is optically non-transparent.

2. The wearable heart activity sensor device of claim 1, further comprising at least one skin measurement electrode arranged on the substrate on the opposite side than the at least one LED and the at least one photo sensor.

3. The wearable heart activity sensor device of claim 2, wherein the substrate comprises at least one through hole for a signal line to the at least one electrode.

4. The wearable heart activity sensor device of claim 1, wherein thickness of the substrate is 0.76 millimetres or less.

5. The wearable heart activity sensor device of claim 1, wherein the substrate is of flexible material, and wherein the overmold of thermoplastic material is rigid.

6. The wearable heart activity sensor device of claim 1, further comprising:
    at least one processor external to the overmold of thermoplastic material; and
    signal lines arranged on the substrate inside and outside the overmold to couple the at least one processor to the at least one light emitting diode and the at least one photo sensor.

7. The wearable heart activity sensor device of claim 1, wherein the pairs of LEDs are disposed to different directions from the at least one photo sensor.

8. The wearable heart activity sensor device of claim 1, further comprising at least one display screen on the substrate, wherein the overmold covers the at least one display screen and at least the part of the overmold that covers the display screen is of optically transparent material.

9. A method for manufacturing a wearable heart activity sensor device, comprising:
    obtaining a substrate of optically transparent material arranged to face a skin of a user when the sensor device is worn by the user;
    assembling at least one light emitting diode (LED) of a photoplehysmogram (PPG) sensor on the substrate such that the at least one LED is arranged to emit light through the substrate, wherein the at least one LED comprises a first set of LEDs arranged to emit light at a first wavelength and a second set of LEDs arranged to emit light at a second wavelength different from the first wavelength, and wherein the first set and second set of LEDs are arranged spatially in pairs such that each pair comprises an LED of the first set and an LED of the second set disposed directly next to one another on the substrate, wherein different pairs of LEDs are spatially separated on the substrate;
    assembling at least one photo sensor of the PPG sensor on the substrate as spatially separated from the at least one LED and such that the at least one photo sensor is arranged to absorb light emitted by the at least one LED through the substrate, wherein the at least one LED and the at least one photo sensor are comprised in the PPG sensor of the heart activity sensor device, and wherein the at least one photo sensor comprises a plurality of photo sensors, and wherein at least one pair of LEDs is disposed between the plurality of photo sensors, and wherein at least two pairs of LEDs are disposed between opposite sides of one of the plurality of photo sensor; and
    overmolding the at least one light emitting diode, the at least one photo sensor, a space between the at least one light emitting diode and the at least one photo sensor, and a space between the different pairs of LEDs with optically non-transparent thermoplastic material.

10. The method of claim 9, further comprising:
    assembling at least one skin measurement electrode on the substrate on the opposite side than the at least one LED and the at least one photo sensor;
    forming at least one through hole to the substrate; and
    arranging a signal line to the at least one electrode through the at least one through hole.

11. The method of claim 9, further comprising:
    arranging a plurality of signal lines on the substrate, the plurality of signal lines coupling to the at least one LED and the at least one photo sensor;
    arranging the overmold to cover the signal lines only partially; and
    after said overmolding, coupling exposed parts of the signal lines to at least one electronic component external to the overmold.

12. The method of claim 9, further comprising thermoforming the substrate before assembling the at least one LED and the at least one photo sensor on the substrate.

* * * * *